United States Patent

Logothetis et al.

[11] Patent Number: 5,823,044
[45] Date of Patent: Oct. 20, 1998

[54] METHOD FOR SELECTIVE GAS SENSORS BASED ON NONLINEAR GAS REACTIONS

[75] Inventors: Eleftherios M. Logothetis, Birmingham; Michael D. Hurley, Ann Arbor; Richard E. Soltis, Saline, all of Mich.

[73] Assignee: Ford Global Technologies, Inc., Dearborn, Mich.

[21] Appl. No.: 848,333

[22] Filed: Apr. 30, 1997

[51] Int. Cl.⁶ .................... G01N 7/00; G01N 27/00
[52] U.S. Cl. .................................. 73/23.2; 422/98
[58] Field of Search .................. 73/23.2, 23.31, 73/31.05, 31.06; 422/98, 94, 88; 204/425

[56] References Cited

U.S. PATENT DOCUMENTS

| | | | |
|---|---|---|---|
| 4,399,684 | 8/1983 | Advani et al. . | |
| 4,542,640 | 9/1985 | Clifford . | |
| 4,627,269 | 12/1986 | Forster et al. | 73/31.06 |
| 4,703,646 | 11/1987 | Müller et al. | 73/24.01 |
| 5,027,646 | 7/1991 | Mizutani et al. | 73/118.1 |
| 5,047,352 | 9/1991 | Stetter et al. | 436/181 |
| 5,265,417 | 11/1993 | Visser et al. . | |
| 5,451,371 | 9/1995 | Zanini-Fisher et al. . | |
| 5,527,446 | 6/1996 | Kosek et al. . | |
| 5,595,647 | 1/1997 | Hoetzel et al. | 205/784.5 |

FOREIGN PATENT DOCUMENTS 9300581  1/1993  European Pat. Off. .

*Primary Examiner*—Hezron E. Williams
*Assistant Examiner*—Jay L. Politzer
*Attorney, Agent, or Firm*—Lorraine S. Melotik, Esq.; Roger L. May, Esq.

[57] ABSTRACT

A method for determining an amount of a gas of interest contained in a measurement gas includes the steps of periodically modulating a specified flux of a measurement gas at a first predetermined frequency, periodically modulating a specified flux of a specified gas that can react non-linearly with the gas of interest at a second predetermined frequency, adding the modulated flux of the specified gas to the modulated flux of the measurement gas, passing the mixture of the two modulated gas fluxes through a reactor where the gas of interest reacts with the specified gas to produce a third gas, exposing a gas sensor that can respond to the third gas present in the gas mixture after the reactor, measuring the sensor output at zero frequency (DC) and at specified frequencies (AC), and determining the original concentration of the gas of interest in the measurement gas from the measured sensor output at zero frequency and at the specified frequencies.

3 Claims, 1 Drawing Sheet

METHOD FOR SELECTIVE GAS SENSORS BASED ON NONLINEAR GAS REACTIONS

BACKGROUND OF THE INVENTION

1. Field of the Invention

The present invention relates generally to gas sensors and, more specifically, to a method for determining an amount of a gas of interest contained in a measurement gas based on non-linear gas reactions.

2. Description of the Related Art

In recent years, gas sensors are finding an ever increasing use in many applications including combustion regulation, process control, protection against hazards, and health related applications. In the automotive industry, for example, zirconium oxide ($ZrO_2$) based oxygen sensors have been used for many years for on-board vehicle air/fuel (A/F) control and for monitoring applications. Tin oxide ($SnO_2$) based sensors are being used for detecting explosive mixtures such as methane ($CH_4$) and hydrogen ($H_2$) in air and toxic gases such as carbon monoxide (CO).

One of the main limitations of existing gas sensors is that most of them are not selective, i.e. they respond not only to the gas of interest but also to other gases. This lack of selectivity creates problems in using these gas sensors. For example, in protecting against CO poisoning, a gas sensor must be capable of responding in the 10–100 parts per million (ppm) range of CO. $SnO_2$ based sensors, however, respond not only to these CO levels but also to similar levels of other gases such as $H_2$ and $CH_4$. Consequently, a false alarm can be generated by these $SnO_2$ sensors when the ambient air contains, for example, 1000 ppm $H_2$, which presents no adverse health effect to humans. Another example for the need to have selective gas sensors, i.e., sensors responding only to a specific gas, relates to the field of automotive vehicle diagnostics. Federal and state regulations require the on-board vehicle monitoring of the efficiency of the so called Three-Way-Catalyst (TWC) in oxidizing hydrocarbons (HC). For successful use in this application, a HC gas sensor must not respond to CO because the concentrations of CO in the exhaust gas of an automotive vehicle are generally considerably higher than those of the hydrocarbons.

A great deal of research and development has been expended in the last 10–20 years to improve the selectivity of existing gas sensors or to develop new more selective gas sensors. Much of this work was devoted to developing new sensing materials or modifying the properties of existing materials. For example, many modifications of $SnO_2$ have been reported either of its surface or of its bulk, e.g., by doping with a variety of ions. This approach has helped in some cases but the selectivity problem still remains. Several other methods purporting selectivity have been reported as discussed below.

One method, currently under extensive investigation is the use of "physical" filters to separate the gaseous molecule of interest. Many materials are being developed that have controlled porosity with pore diameters in the few Angstroms range or channels with well defined size also in the few Angstroms range. Examples of the later type of materials are the well known zeolites.

Another method is to use a "chemical" filter to remove the interfering gas before it reaches the nonselective sensor. For example, Logothetis et al. (Proc. of 2nd Intern. Meeting on Chemical Sensors, p.175, Bordeaux, France 1986) discloses a sensor for $CH_4$ which did not respond to other gases such as CO, $H_2$, alcohols, HC (e.g. alkanes) and other oxidizable gases. This sensor used a platinum (Pt) catalyst placed before a nonselective sensor such as a $SnO_2$ sensor and heated to a temperature of less than 500° C. At these temperatures, all the above-mentioned gases are catalytically oxidized and removed by the Pt catalyst except $CH_4$, that needs higher temperatures for its catalytic oxidation on Pt. Consequently, if the ambient atmosphere contains $CH_4$ and other oxidizable gases, the interfering gases are removed as they diffuse through the Pt catalyst and only $CH_4$ reaches the $SnO_2$ sensor. This method is effective but is applicable only to a few cases.

Another method which is presently under extensive study is to use an array of several nonselective gas sensors which respond to the gas of interest x and to several other gases y, but with different sensitivities. By including a sufficient number of gas sensors in the array, one can, in principle, detect the presence of molecule x in the ambient air by solving a set of equations describing the response of each sensor to the gases x and y. In practice, however, this analysis may not be unambiguous. Therefore, there is a need in the art to develop other methods for making selective gas sensors.

In a co-pending patent application, the inventors described a method of introducing selectivity to a nonselective gas sensor for determining the amount of a gas of interest contained in a measurement gas wherein the nonselective gas sensor responds not only to the gas of interest but also to other interfering gases contained in the measurement gas. The method included the steps of periodically modulating a specified flux of a measurement gas at a first predetermined frequency, periodically modulating a specified flux of a gas of interest at a second predetermined frequency, and adding the modulated flux of the gas of interest to the modulated flux of the measurement gas. The method also included exposing a nonselective gas sensor to the combination of the modulated flux of the measurement gas and the modulated flux of the gas of interest, measuring a sensor output of the nonselective gas sensor at zero frequency (DC) and at frequencies related to the first and second predetermined frequencies (AC), and determining an original concentration of the gas of interest in the measurement gas from the measured sensor output at zero frequency and at frequencies related to the first and second predetermined frequencies.

However, the above method is not applicable to all nonselective gas sensors and to all gases of interest. Thus, there is still a need in the art for more methods for introducing selectivity to nonselective gas sensors.

It is known in the art, that a method for measuring the concentration of a molecule X in the absence of a gas sensor responding directly to X is based on reacting X with another molecule Y and measuring the concentration of a specific product Z of the reaction

with an appropriate gas sensor. The usefulness of this method, however, is limited to the cases where only the chemical species of interest produces the reaction product detected by the gas sensor and the gas sensor does not respond to any other chemical species present in the incoming (measurement) gas or in the other products of the reaction. Thus, there is a need in the art for a method which, under certain conditions, removes these limitations. This method is based on the rate of production of species Z being a nonlinear function of X (or Y).

SUMMARY OF THE INVENTION

Accordingly, the present invention is a method for determining an amount of a gas of interest contained in a measurement gas including the steps of periodically modulating a specified flux of a measurement gas at a first predetermined frequency and periodically modulating a specified flux of a specified gas that can react non-linearly with the gas of interest at a second predetermined frequency. The method also includes the steps of adding the modulated flux of the specified gas to the modulated flux of the measurement gas and passing the mixture of the two modulated gas fluxes through a reactor where the gas of interest reacts with the specified gas to produce a third gas. The method further includes the steps of exposing a sensor that can respond to the third gas present in the gas mixture after the reaction, measuring the sensor output at zero frequency (DC) and at specified frequencies (AC), and determining the original concentration of the gas of interest in the measurement gas from the measured sensor output at zero frequency and at the specified frequencies.

One feature of the present invention is that selectivity is provided to a non-selective gas sensor. Another feature of the present invention is that the nonselective gas sensor achieves selectivity in response to non-linear gas reactions.

Other features and advantages of the present invention will be readily appreciated as the same becomes better understood after reading the subsequent description when considered in connection with the accompanying drawings.

DESCRIPTION OF THE PREFERRED EMBODIMENT(S)

Figure 1:
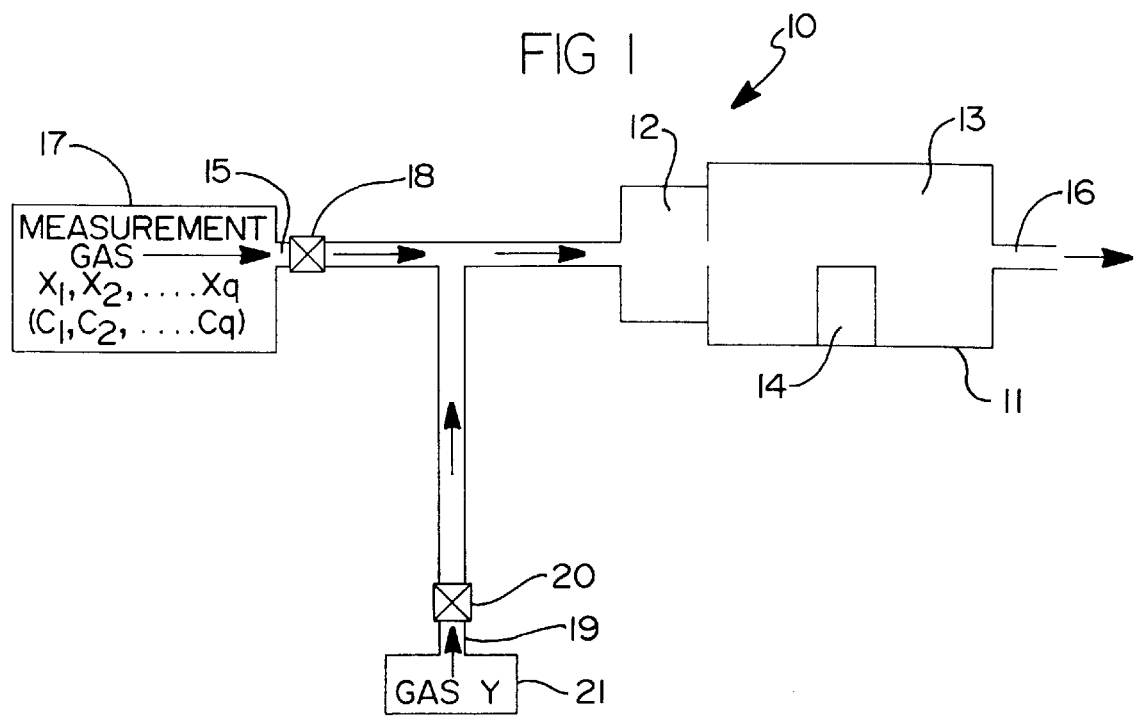
FIG. 1 is a schematic of one embodiment of the prior art used to detect and measure the concentration of a gas X in the measurement gas by adding, to the measurement gas a gas Y which reacts with gas X to give gas Z, and using a sensor which responds only to Z to measure the concentration of gas Z and from that to deduce the concentration of gas X.

It is known in the prior art that one method for measuring a gas $X_1$ in the measurement gas when there is no convenient sensor that can measure gas $X_1$ is to add to the measurement gas another gas Y which reacts with gas $X_1$ and then measure a product of reaction Z. FIG. 1 illustrates an embodiment of an apparatus 10 of the prior art. The apparatus 10 includes a structure 11 having a reactor 12 and a chamber 13 in which a gas sensor 14 is placed. The apparatus 10 includes an inlet 15 and an outlet 16 connected to the structure 11 to allow a measurement gas 17 containing gas $X_1$ to enter the reactor 12, reach the gas sensor 14, and exit the structure 11 through the outlet 16. The apparatus 10 also includes a flowmeter 18 to control the flux $F_o$ of the measurement gas 17 entering the structure 11. The apparatus 10 includes a second inlet 19 to allow a known flux $F_y$ of a gas Y from a source 21 to be added and mixed with flux $F_o$ before the reactor 12. The apparatus 10 further includes a flowmeter 20 to control the flux $F_y$.

For the method of the prior art, the mixture of the measurement gas 17 and the added gas Y enter the reactor 12 where gas Y reacts with gas $X_1$ to give a product of reaction Z. The amount of Z produced in the reactor 12 is measured with the sensor 14 in the chamber 13. The unknown concentration of gas $X_1$ in the measurement gas 17 is determined from the measurement of the concentration of gas Z after calibration of the apparatus 10. A well known example of the apparatus 10 of the prior art is the $NO_x$ Analyzer used in engine dynamometers to measure the concentration of NO and $NO_2$ in the exhaust gas from an internal combustion engine (not shown).

The above method using the apparatus 10 of the prior art is not useful when the measurement gas 17 contains not only gas $X_1$ but also other gases $X_2, X_3, \ldots, X_q$, and the sensor 14 is not selective to gas Z; that is, the sensor 14 responds not only to gas Z but also to one or more of the gases $X_2, X_3, \ldots, X_q$. The method is also not useful when the sensor 14 is specific to gas Z and one or more of gases $X_2, X_3, \ldots, X_q$ react with gas Y to give gas Z. These limitations of the prior art are removed, under certain conditions, by a method, according to the present invention, to be described.

Suppose that the measurement gas contains the gas of interest $X_1$ and other gases $X_2, X_3, \ldots, X_q$, and that no sensor exists that can detect and measure $X_1$. But a sensor exists that can measure a gas Z which can be produced when gas $X_1$ reacts with a gas Y. According to a method of the present invention, a specified flux $F_o$ of the measurement gas is periodically modulated at some frequency $\omega$. A specified flux $F_y$ of a gas Y is periodically modulated at some frequency $\omega$ and added to the modulated flux $F_o$. The mixture of the two modulated fluxes is sent though a reactor where gas Y reacts nonlinearly with the gas of interest $X_1$ and also reacts with one or more of the other gases $X_2, X_3, \ldots, X_q$ in the measurement gas. The gas exiting the reactor is passed by the sensor which responds to gas Z and possibly to some of the other gases $X_2, X_3, \ldots, X_q$ and to some of the other products of reaction. The sensor response is measured and the DC (zero frequency) and the AC (at various specified frequencies) components of the response are separated by appropriate electronic circuitry well known in the art. The original concentration of the unknown gas of interest in the measurement gas can be determined from the DC and AC components of the sensor response.

Figure 2:
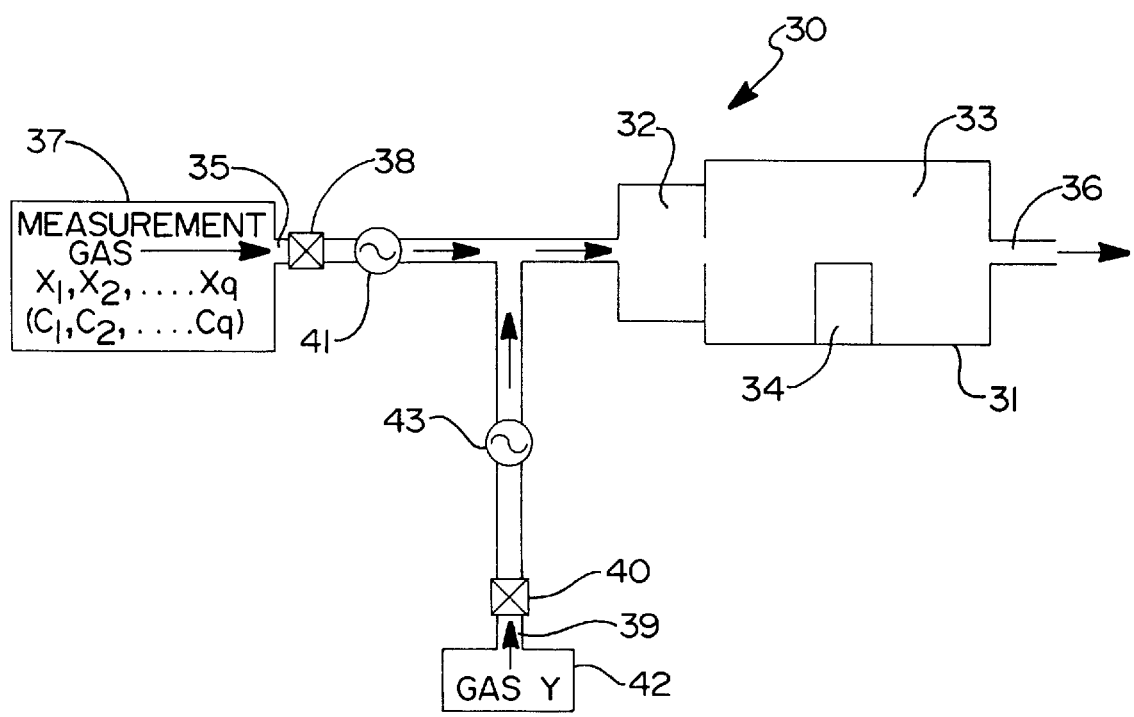
FIG. 2 is a schematic view of one embodiment used to practice a method, according to the present invention, to measure the concentration of gas X in the measurement gas by modulating the measurement gas, by adding to the measurement gas a modulated gas Y which reacts nonlinearly with gas X to product gas Z, and by using a nonselective sensor to measure gas Z and determine the concentration of gas X.

One embodiment of an apparatus 30, according to the present invention, is illustrated in FIG. 2. The apparatus 30 includes a structure 31 having a reactor 32 and a chamber 33 in which a gas sensor 34 is placed. The apparatus 30 also includes an inlet 35 and an outlet 36 connected to the structure 31 to allow a measurement gas 37 containing gas $X_1$ to enter the reactor 32, reach the gas sensor 34, and exit the structure 31 through the outlet 36. The apparatus 30 includes a flowmeter 38 which is used to control the flux $F_o$ of the measurement gas 37 entering the structure 31 and a modulator 41 which is used to time-modulate flux $F_o$. The modulator 41 can be a solenoid valve which is periodically opened and closed at some specified frequency $\omega$. Alternatively, modulator 41 can be an electronic mass flow controller. The apparatus 30 further includes a second inlet 39 through which a known flux $F_y$ of gas Y is added and mixed with flux $F_o$ before the reactor 32. The apparatus 30 includes a suitable source 42, e.g. a gas cylinder containing gas Y, for the flux $F_y$ of gas Y. The apparatus 30 includes a flowmeter 40 which is used to control the flux $F_y$ of the gas Y from the source 42 entering the structure 31 and a modulator 43 which is used to time-modulate flux $F_y$. The modulator 43 can be a solenoid valve which is periodically opened and closed at some specified frequency $\omega$ generally different from the frequency of the modulator 41. Alternatively, the modulator 43 can be an electronic mass flow controller. The mixture of the measurement gas 37 and the added gas Y from the source 42 enter the reactor 32 where gas Y reacts with gas $X_1$ to give a product of reaction Z. The amount of Z produced in the reactor 32 is measured with the sensor 34 in the chamber 33. The unknown concentration of gas $X_1$ in the measurement gas 37 is determined from the measurement of the concentration of gas Z after calibration of the apparatus 30.

To illustrate how the present invention can measure, unambiguously, the concentration of the gas of interest $X_1$ when the gas sensor 34 is used, several examples will be discussed. It is emphasized, however, that these examples are given only for the purpose of illustration and do not impose limitations on the present invention. These examples will also demonstrate that, depending on the type of the sensor non-linearity, the modulation of both the flux of the measurement gas 37 and the flux of the added gas $X_1$ is not necessary. In these cases, modulation of the flux $F_o$ only without addition of $F_y$, or modulation only of the added flux $F_y$ is sufficient.

EXAMPLE 1

Consider the measurement gas 37 consisting of the gas of interest $X_1$ and other gases $X_2, X_3, \ldots, X_q$. $X_1$ can react with a gas Y to give a gas Z as a product of the reaction. Some of the other gases $X_2, X_3, \ldots, X_q$ may react with Y but none of their reaction products is Z. A sensor exists which can measure selectively Z, that is, the sensor responds only to gas Z. In this case, the prior art method used with the apparatus 10 illustrated in FIG. 1 can be used to unambiguously measure $X_1$.

EXAMPLE 2

Consider the measurement gas 37 consisting of the gas of interest $X_1$ and other gases $X_2, X_3, \ldots, X_q$ with concentrations $C_1, C_2, C_3, \ldots, C_q$. $X_1$ can react with a gas Y to give a gas Z as a product of the reaction. One or more of the other gases $X_2, X_3, \ldots, X_q$ can also react with Y and one of their reaction products is Z. A sensor exists which responds to Z linearly. In addition, the sensor can measure Z selectively, that is, the sensor responds only to gas Z. Although the sensor is selective, the prior art method used with the apparatus 10 in FIG. 1 cannot be used to unambiguously measure the concentration $C_1$ of gas $X_1$.

Consider in addition that the reaction between $X_1$ and Y is nonlinear whereas the reactions between Y and the other gases $X_2, X_3, \ldots, X_q$ are linear. For example, the rate of formation of product Z is $$R(Z) = a_1 C_1^2 C_y + a_2 C_2 C_y + \ldots + a_q C_q C_y \qquad \text{(Eq. 1)}$$

If the measurement gas 37 entering the apparatus 30 is modulated at frequency $\omega$, the concentration of each gas $X_1$, $X_2, \ldots, X_q$ in flux $F_o$ is also modulated. For example, if the modulation is sinusoidal and one hundred percent (100%), the concentration of the gases $X_1, X_2, \ldots, X_q$ in the flux $F_o$ of the measurement gas 37 varies with time as $$(C_1/2)(1-\sin \omega t), (C_2/2)(1-\sin \omega t), \ldots, (C_q/2)(1-\sin \omega t) \qquad \text{(Eq. 2)}$$

Substituting these in Eq. 1 to obtain the rate of production Z, one obtains for the concentration $C_z$ of gas Z the expression $$C_z = A[a_1(C_1/2)^2(1-\sin \omega t)^2 + a_2(C_2/2)(1-\sin \omega t) + a_q(C_q/2)(1-\sin \omega t)]C_y \qquad \text{(Eq. 3)}$$

Since the response S of the gas sensor 34 to gas Z is linear $$S = BC_z$$

the gas sensor 34 response to the modulated measurement gas 37 is $$S = AB[a_1(C_1/2)^2(1-\sin \omega t)^2 + a_2(C_2/2)(1-\sin \omega t) + a_q(C_q/2)(1-\sin \omega t)]C_y \qquad \text{(Eq. 4)}$$

After carrying out the algebra in Eq. 4, one obtains $$\begin{aligned} S &= (AB/2)[3/4 a_1 C_1^2 + a_2 C_2 + \ldots + a_q C_q]C_y - \\ &\quad (AB/2)[a_1 C_1^2 + a_2 C_2 + \ldots + a_q C_q]C_y \sin \omega t - \\ &\quad (AB/8) a_1 C_1^2 C_y \cos 2\omega t = \\ &= S(0) + S(\omega)\sin \omega t + S(2\omega)\cos 2\omega t \end{aligned} \qquad \text{(Eq. 5)}$$

If the gas sensor 34 output at frequency $2\omega$, $S(2\omega)$, is measured, the unknown concentration $C_1$ of gas $X_1$ can be unambiguously determined from $$S(2\omega) = (AB/8) a_1 C_1^2 C_y \qquad \text{(Eq. 6)}$$

The constants A and B are obtained by prior calibration of the gas sensor 34. It should be appreciated that, in this example, it is not necessary to also modulate the added gas Y.

EXAMPLE 3

Consider the case of Example 2 except that the reaction rate $R(Z)$ of production of gas Z is given not by Eq. 1 but by Eq. 7:

$$R(Z) = a_1 C_1 C_y^2 + a_2 C_2 C_y + \ldots + a_q C_q C_y \qquad \text{(Eq. 7)}$$

If one modulates only the measurement gas 37, $C_1$ cannot be determined. On the other hand, if one modulates only the added gas Y at frequency $\omega$ $$C_y = C(1 - \sin \omega t) \qquad \text{(Eq. 8)}$$

the concentration of gas Z reaching the gas sensor 34 is:

$$C_z = A[a_1 C_1 C^2(1-\sin \omega t)^2 + a_2 C_2 C(1-\sin \omega t) + \ldots + a_q C_q C(1-\sin \omega t)] \qquad \text{(Eq. 9)}$$

The response of the sensor is then $$\begin{aligned} S &= AB[(3/2) a_1 C_1 C^2 + a_2 C_2 C + \ldots + a_q C_q C] - AB[2 a_1 C_1 C^2 + a_2 C_2 C + \ldots + \\ &\quad + a_q C_q C]\sin \omega t - (AB/2) a_1 C_1 C^2 \cos(2\omega t) = \\ &= S(0) + S(\omega)\sin \omega t + S(2\omega)\cos(2\omega t) \end{aligned} \qquad \text{(Eq. 10)}$$

If the gas sensor 34 output at frequency $2\omega$, $S(2\omega)$, is measured, the unknown concentration $C_1$ of gas $X_1$ can be unambiguously determined from $$S(2\omega) = (AB/2) a_1 C_1 C^2 \qquad \text{(Eq. 11)}$$

EXAMPLE 4

Consider the case where not only gas $X_1$ but also gases $X_2$ and $X_3$ react non-linearly with gas Y to give a gas Z with the rate of production of gas Z given by $$R(Z)=a_1C_1^2C_y^2+a_2C_2^2C_y+a_3C_3C_y^2+a_4C_4C_y \quad \text{(Eq. 12)}$$

It is apparent that modulating only the measurement gas 37 as in Example 2 or only the added gas Y as in Example 3 will not allow the unambiguous determination of the unknown concentration $C_1$ of gas $X_1$. However, this can be accomplished if we modulate both, the measurement gas at frequency ω (Eq. 2) and the gas Y at frequency ώ (Eq. 8). In this case, the concentration of gas Z is given by $$C_z = A\,[a_1(C_1/2)^2(1-\sin\omega t)^2 C^2(1-\sin\acute{\omega}t)^2 + \quad \text{(Eq. 13)}$$
$$+ a_2(C_2/2)^2(1-\sin\omega t)^2 C(1-\sin\acute{\omega}t) +$$
$$+ a_3C_3(1-\sin\omega t)C^2(1-\sin\acute{\omega}t)^2 +$$
$$+ a_4C_4(1-\sin\omega t)C_y(1-\sin\acute{\omega}t)]$$

The output of a gas sensor 34 that responds to gas Z linearly is $$S(Z)=BC_z \quad \text{(Eq. 14)}$$

Substituting Eq. 13 into Eq. 14 and carrying out the algebra, the first term becomes $$ABa_1(C_1/2)^2C^2(1-2\sin\omega t+\sin{}^2\omega t-\sin\acute{\omega} t+2\sin\omega t\sin\acute{\omega} t-\sin{}^{2}\acute{\omega} t\sin\omega t+$$
$$\sin{}^2\acute{\omega} t-2\sin\omega t\sin{}^2\acute{\omega} t+\sin{}^2\omega t\sin{}^2\acute{\omega} t) \quad \text{(eq. 15a)}$$

The second term becomes $$ABa_2(C_2/2)^2C(1-2\sin\omega t+\sin{}^2\omega t-\sin\acute{\omega} t+2\sin\omega t\sin\acute{\omega} t-\sin{}^2\omega t\sin\acute{\omega} t) \quad \text{(Eq. 15b)}$$

The third term becomes $$ABa_3C_3C^2(1-\sin\omega t-2\sin\omega t+2\sin\omega t\sin\acute{\omega} t+\sin{}^2\acute{\omega} t-\sin\omega t\sin{}^2\acute{\omega} t) \quad \text{(Eq. 15c)}$$

And the fourth term becomes $$ABa_4C_4C(1-\sin\omega t-\sin\acute{\omega} t+\sin\omega t\sin\acute{\omega} t) \quad \text{(Eq. 15d)}$$

It is apparent that the gas sensor 34 output S(Z) has a DC component and components at several frequencies, e.g. ω, ώ, 2ω, 2ώ, ω+ώ, ω−ώ, 2ω+ώ, and several others. Most of these components have contribution from all four input gases $X_1$, $X_2$, $X_3$, and $X_4$. The only components which have contribution only from gas $X_1$ are some of the ones that arise from the last term in Eq. 15a, $\sin^2\omega t\,\sin^2\acute\omega t$. Since $\sin^2 x=\tfrac{1}{2}(1-\cos 2x)$, we obtain for this term $(¼)(1-\cos 2\omega t-\cos 2\acute\omega t+\cos 2\omega t\cos 2\acute\omega t)$.

The last term $\cos 2\omega t\cos 2\acute\omega t$ is equal to $(½)(\cos(2\omega+2\acute\omega)t+\cos(2\omega-2\acute\omega)t)$.

It is apparent that the sensor output S(Z) has a component at frequency $2\omega+2\acute\omega$ given by $$S(2\omega+2\acute\omega)=ABa_1(C_1/2)^2C^2 \quad \text{(Eq. 16)}$$

from which the unknown concentration $C_1$ of gas $X_1$ can be determined unambiguously.

EXAMPLE 5

Consider again the case of Example 2 where the rate of production of Z is given by Eq. 1.

$$R(Z)=a_1C_1^2C_y+a_2C_2^2C_y+\ldots+a_qC_qC_y \quad \text{(Eq. 1)}$$

However, in this example, the gas sensor 34 response to Z is not linear, e.g. it is quadratic, $$S(C_z)=BC_z^2 \quad \text{(Eq. 17)}$$

If, as in Example 2, we modulate the flux $F_o$ of the measurement gas at frequency ω, the concentration of gas Z is $$C_z=C_z(0)+C_z(\omega)\sin\omega t+A/8 a_1C_1^2C_y\cos 2\omega t \quad \text{(Eq. 18)}$$

where $C_z(0)$ and $C_z(\omega)$ have contributions from all gases $X_1$, $X_2$, ..., $X_q$. The response of the gas sensor 34 is then, $$S=B[C_z(0)+C_z(\omega)\sin\omega t+A/8 a_1C_1^2C_y\cos 2\omega t]^2 \quad \text{(Eq. 19)}$$

If we expand Eq. 19, we obtain a term $$((A/8)a_1C_1^2C_y)^2\cos{}^2 2\omega t$$

Since $\cos^2 2\omega t=(½)(1+\cos 4\omega t)$, the gas sensor 34 response $S(C_z)$ contains a component at frequency 4ω

$$S(4\omega)=(½)(A/8 a_1C_1^2C_y)^2 \quad \text{(Eq. 20)}$$

from which the unknown concentration $C_1$ of gas $X_1$ can be determined unambiguously.

EXAMPLE 6

Consider the case where the gas sensor 34 responds not only to Z but also to other gases $X_2$, ..., $X_q$ or to products $Z_2$, ..., $Z_q$ of the reactions between Z and the other gases $X_2$, ..., $X_q$. For example, consider the case that the gas sensor 34 response is $$S=BC_z+L_2C_2+L_3C_3 \quad \text{(Eq. 21)}$$

and that gas Y reacts only with gas $X_1$ to give gas Z:

$$R(Z)=a_1C_1^2C_y \quad \text{(Eq. 22)}$$

If we modulate the added flux of gas Y at frequency ω, $C_y=C(1-\sin\omega t)$, the concentration of gas Z is $$C_z=Aa_1C_1^2C(1-\sin\omega t) \quad \text{(Eq. 23)}$$

The response of the gas sensor 34 is $$S=ABa_1C_1^2C(1-\sin\omega t)+L_2C_2+L_3C_3$$

or $$S=[ABa_1C_1^2C+L_2C_2+L_3C_3]-ABa_1C_1^2C\sin\omega t=$$
$$\equiv S(0)+S(\omega)\sin\omega t \quad \text{(Eq. 24)}$$

If the gas sensor 34 output at frequency ω is measured, the unknown concentration $C_1$ of gas $X_1$ can be unambiguously determined from $$S(\omega)=ABa_1C_1^2C \quad \text{(Eq. 25)}$$

The present invention has been described in an illustrative manner. It is to be understood that the terminology which has been used is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. A method for determining an amount of gas of interest contained in a measurement gas, said method comprising the steps of:

periodically modulating a specified flux of a measurement gas at a first predetermined frequency;

periodically modulating a specified flux of a specified gas that can react non-linearly with a gas of interest at a second predetermined frequency;

adding the modulated flux of the specified gas to the modulated flux of the measurement gas;

passing the mixture of the two modulated gas fluxes through a reactor where the gas of interest reacts with the specified gas to produce a third gas;

exposing a gas sensor that can respond to the third gas present in the gas mixture after the reactor;

measuring the sensor output at zero frequency (DC) and at specified frequencies (AC); and determining the original concentration of the gas of interest in the measurement gas from the measured sensor output at zero frequency and at the specified frequencies.

2. A method for determining an amount of gas of interest contained in a measurement gas, said method comprising the steps of:

periodically modulating a specified flux of a measurement gas at a predetermined frequency;

adding a specified gas that can react non-linearly with a gas of interest to the modulated flux of the measurement gas;

passing the mixture of the two gases through a reactor where the gas of interest reacts with the specified gas to produce a third gas;

exposing a gas sensor that can respond to the third gas present in the gas mixture after the reactor;

measuring the sensor output at zero frequency (DC) and at specified frequencies (AC); and determining the original concentration of the gas of interest in the measurement gas from the measured sensor output at zero frequency and at the specified frequencies.

3. A method for determining an amount of gas of interest contained in a measurement gas, said method comprising the steps of:

providing a measurement gas;

periodically modulating a specified flux of a specified gas that can react nonlinearly with a gas of interest at a predetermined frequency;

adding the modulated flux of the specified gas to the measurement gas;

passing the mixture of the two gases through a reactor where the gas of interest reacts with the specified gas to produce a third gas;

exposing a gas sensor that can respond to the third gas present in the gas mixture after the reactor;

measuring the sensor output at zero frequency (DC) and at specified frequencies (AC); and determining the original concentration of the gas of interest in the measurement gas from the measured sensor output at zero frequency and at the specified frequencies.

* * * * *